(12) United States Patent
Maser et al.

(10) Patent No.: US 10,687,885 B2
(45) Date of Patent: Jun. 23, 2020

(54) METHOD AND DEVICE FOR CONTROLLING AN ELECTROSURGICAL HF APPARATUS AND HF APPARATUS

(71) Applicant: Aesculap AG, Tuttlingen (DE)

(72) Inventors: Thomas Maser, Zimmern ob Rottweil (DE); Heiko Reichle, Tuttlingen (DE); Anton Keller, Dürbheim (DE); Stefan Eick, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 483 days.

(21) Appl. No.: 15/021,485

(22) PCT Filed: Sep. 10, 2014

(86) PCT No.: PCT/EP2014/069315
§ 371 (c)(1),
(2) Date: Mar. 11, 2016

(87) PCT Pub. No.: WO2015/036444
PCT Pub. Date: Mar. 19, 2015

(65) Prior Publication Data
US 2016/0220299 A1    Aug. 4, 2016

(30) Foreign Application Priority Data
Sep. 16, 2013   (DE) .......... 10 2013 110 172

(51) Int. Cl.
*A61B 18/12*    (2006.01)
*A61B 18/00*    (2006.01)
(Continued)

(52) U.S. Cl.
CPC ...... *A61B 18/1233* (2013.01); *A61B 18/1206* (2013.01); *A61B 2017/00132* (2013.01);
(Continued)

(58) Field of Classification Search
CPC .... A61B 2018/1293; A61B 2090/0803; A61B 2090/0804; A61B 2090/0805;
(Continued)

(56) References Cited

U.S. PATENT DOCUMENTS

| 4,655,215 A | 4/1987 | Pike |
| 4,860,745 A | 8/1989 | Farin et al. |

(Continued)

FOREIGN PATENT DOCUMENTS

| CN | 101605491 A | 12/2009 |
| DE | 1146989 | 7/1959 |

(Continued)

OTHER PUBLICATIONS

German search report dated Mar. 17, 2014 for German Application No. 10 2013 110 172.0 with translation.
(Continued)

*Primary Examiner* — Jaymi E Della
*Assistant Examiner* — Rachel A. Vierra (57) ABSTRACT

A method of controlling an electrosurgical HF apparatus, as well as an HF apparatus, includes an electrosurgical instrument and an HF generator for generating an HF current. The HF generator is in a locked state in which its activation is not possible. An application to be carried out is to be selected prior to a user-side activation of the HF generator, whereby the HF generator is unlocked.

17 Claims, 4 Drawing Sheets

(51) Int. Cl.
*A61B 17/00* (2006.01)
*A61B 34/00* (2016.01)
(52) U.S. Cl.
CPC ............ *A61B 2017/00477* (2013.01); *A61B 2017/00482* (2013.01); *A61B 2018/00601* (2013.01); *A61B 2018/00642* (2013.01); *A61B 2018/00708* (2013.01); *A61B 2018/00898* (2013.01); *A61B 2034/256* (2016.02); *A61B 2560/0493* (2013.01)
(58) Field of Classification Search
CPC ........ A61B 2090/0806; A61B 18/1233; A61B 18/1206; A61B 2034/256; A61B 2017/00132; A61B 2017/00477; A61B 2017/00482; A61B 2018/00601; A61B 2018/00642; A61B 2018/00708; A61B 2018/00898; A61B 2560/0493; A61N 1/1605; A61N 1/36142; A61N 1/372; A61N 1/37247
See application file for complete search history.

(56) References Cited

U.S. PATENT DOCUMENTS

| | | | |
|---|---|---|---|
| 5,035,695 A | 7/1991 | Weber | |
| 8,147,485 B2* | 4/2012 | Wham | A61B 18/1206 |
| | | | 606/34 |
| 9,192,289 B2 | 11/2015 | Umemoto et al. | |
| 2004/0015163 A1* | 1/2004 | Buysse | A61B 18/1206 |
| | | | 606/34 |
| 2006/0020261 A1* | 1/2006 | Refior | A61B 18/1206 |
| | | | 606/34 |
| 2009/0131929 A1* | 5/2009 | Shimizu | A61B 17/320092 |
| | | | 606/34 |
| 2009/0270852 A1 | 10/2009 | Takashino et al. | |
| 2011/0045680 A1 | 2/2011 | Beller | |
| 2012/0316573 A1* | 12/2012 | Durant | A61B 19/2203 |
| | | | 606/130 |
| 2014/0024890 A1 | 1/2014 | Umemoto et al. | |

FOREIGN PATENT DOCUMENTS

| | | |
|---|---|---|
| DE | 102007061483 | 7/2009 |
| EP | 0717967 A2 | 6/1996 |
| EP | 2111812 A2 | 10/2009 |
| EP | 2127590 A1 | 12/2009 |
| EP | 2168517 | 3/2010 |
| JP | H08229050 A | 9/1996 |
| JP | 2008194303 A | 8/2008 |
| JP | 2009261907 A | 11/2009 |
| WO | 2009149799 | 12/2009 |

OTHER PUBLICATIONS

European Office Action for European Application No. 14 766 147.4, dated Jun. 21, 2017, including English translation, 11 pages.

Notification of Reasons for Refusal for Japanese Application No. 2016-541922, dated May 8, 2018, including English translation, 6 pages.

Chinese Office Action for Chinese Application No. 201480050841.1, dated Dec. 25, 2017, including English translation, 8 pages.

* cited by examiner

METHOD AND DEVICE FOR CONTROLLING AN ELECTROSURGICAL HF APPARATUS AND HF APPARATUS

RELATED APPLICATIONS

This application is the U.S. national phase entry of International Application No. PCT/EP2014/069315, filed Sep. 10, 2014, which claims the benefit of priority of German Application No. DE 10 2013 110 172.0, filed Sep. 16, 2013. The contents of International Application No. PCT/EP2014/069315 and German Application No. DE 10 2013 110 172.0 are incorporated by reference herein in their entireties.

FIELD

The present invention relates to a method and a device for controlling an electrosurgical HF apparatus as well as to an electrosurgical HF apparatus comprising an electrosurgical instrument and an HF generator for generating an HF current.

BACKGROUND

Surgical HF apparatuses are commonly known. As part of high-frequency surgery, they are increasingly applied apart from standard applications such as cutting or coagulating in further fields such as for closing hollow organs, connecting biological tissue or in the context of an ablation. In doing so, an electrosurgical instrument directs a high-frequency current (HF current) through tissue to be treated, which is altered thereby. In the course of these special applications, the HF delivery is automatically controlled, metered and ended by an HF generator to which the instrument is electrically connected, and not by the surgeon.

If in the context of the above-mentioned applications of ever increasing variety the electrosurgical instrument is to be variably applicable for differing types of tissue (small intestine, large intestine, rectum, stomach, esophagus), for varying numbers of tissue layers or different application types (resection, anastomosis), it is a must that there is the possibility to be able to make pre-adjustments on the associated HF generator/electrical current source, so that it can make specific or special process settings for the respective application. A wrong setting of certain process parameters may lead in some circumstances to an unsatisfactory result or even to damages on the patient. This is why it has to be ensured at any time that all process parameters are correctly adjusted before an activation of the apparatus.

The concepts for HF activation, i.e. for supplying the HF current to the instrument, are a central topic with HF apparatuses and are known from prior art. An HF activation without a corresponding operation by the user is prevented by various safety functions on the electrosurgical instrument and/or on the HF generator of the apparatus.

From U.S. Pat. No. 5,035,695, there is known a method and an instrument for electro-cauterizing including locking functions which allow for a safe operation of the instrument in case of manual control. By means of a manually operable slide, an electrode of the instrument can be moved from a rest position where it is retracted into the instrument to a cauterizing position in which it projects from the instrument. Here, a lockout switch automatically disconnects the electrode from an HF current source/HF generator, if it is in the rest position. If the electrode is in the rest position, the slide additionally represents a mechanical locking means for activation switches for the manual activation of the electrode, whereas the activation switches are released by the slide in the cauterizing position and can be manually operated. It is a disadvantage that locking and releasing the instrument is carried out manually by the user without consideration of a generator setting.

From the European patent application EP 2 168 517 A1, there is known a system and a method for the manual locking of hand switches of a manually operated electrosurgical clamp for coagulating and severing tissue. The clamp comprises two mutually movable jaw parts which are to be supplied with electric current for the coagulation of tissue. A hand switch has to be selectively and manually operated by the user of the clamp for its activation. A lockout switch is also to be manually operated by the user of the clamp from a first position in which an operation of the hand switch is possible, to a second position in which an operation of the hand switch and an activation of the clamp are not possible. In an alternative embodiment, both the hand switch and the lockout switch have to be electrically closed in order to allow for an activation of the clamp. It is a disadvantage that the manual locking and releasing of the instrument by the user is likewise performed without any feedback to the generator.

From WO2009/149799 A1 there is known a surgical apparatus for coagulation and/or for cutting biological tissue. It comprises a bipolar clamp with two jaw parts for applying HF current, an activation circuitry and an HF generator. The supply of the HF current to the clamp can be controlled by means of the activation switch. In order to guard against operating errors, the apparatus comprises a safety means which cuts off the supply of electric current to the clamp if its jaw parts assume a position which is unsuitable for coagulation. This is merely to prevent an unintentional activation of the clamp.

Finally, U.S. Pat. No. 4,655,215 discloses a monopolar electrosurgical scalpel including a manual control for selective cutting or coagulating processes, with the option that specific operational modes can be deliberately suppressed. The scalpel comprises a slide switch which can be moved to three different positions by the user and via which an activation switch can be locked or released. In a first position, the activation switch is blocked. In a second position, it is to be operated such that the blade of the scalpel is either provided with a coagulation current or with zero current. In a third position, the activation switch is released, so that the blade of the scalpel is supplied either with a coagulation current or a cutting current or also with zero current. Thus, the manual control ensures that any coagulation or cutting currents can be delivered to the scalpel only after a corresponding release by the surgeon. It is a disadvantage here that the activation/setting is performed manually by the user of the scalpel, without said process being linked with a safety function against a false setting.

If an HF apparatus, as described at the outset, is supposed to be used in numerous different applications, a variable and wide range of selecting process parameters is required. It has to be guaranteed, however, that prior to an HF activation of the apparatus or of the process, namely before suppling the HF current to the instrument, an input or a monitoring of the corresponding process parameters by the user of the apparatus has been made in order to avoid a false generator setting, as the case may be.

In the known solutions, HF instruments or apparatuses are operated with fixed process parameters and/or flows. Depending on the respective application, however, single or several of these parameters (e.g. the level and progression of the HF energy) may vary and have to or would have to be correspondingly adapted in order to successfully carry out the desired operation, on the one hand, and to avoid further damages to the tissue, on the other hand.

Apparatuses are also known which allow for a setting of the intensity of the HF process on the HF generator. This gives the operator the possibility to correct the output of the HF energy (slightly) upwards or downwards. After an alteration of process parameters, all subsequent activations will then be carried out with these parameters until a new setting is made. There is the risk to forget to manually/visually check the process parameters or to adjust them correspondingly, although the conditions or requirements in the applications to be performed subsequently may differ from those of the previous application.

SUMMARY

Based on the previously described prior art, the invention is based on the object to provide a method and a device for controlling an electrosurgical HF apparatus as well as such an HF apparatus, wherein it is ensured that the respectively required setting of the apparatus has been correctly made prior to an activation of the HF apparatus.

This object is achieved on the part of the method by a method of controlling an electrosurgical HF apparatus, said HF apparatus comprising an electrosurgical instrument and an HF generator/an electrical current source for generating/providing an HF current, the HF generator being electrically connected to the electrosurgical instrument to deliver the HF current to the instrument due to a user-side activation, in which method a) the HF generator first is in a locked state in which the HF generator can not be activated by the user, b) starting from step a), an application to be performed with the electrosurgical instrument is (manually) obligatorily set by the user, c) the HF generator, when step b) has been carried out, automatically changing over to an unlocked state in which the HF generator can be or is activated by the user, d) the HF generator and/or the electrosurgical instrument connected thereto is or can be activated by the user for carrying out the desired application, and e) the HF generator automatically changes over to the locked state after the user-side activation in step d).

Further, the object is achieved on the part of the device by an electronic control unit of a (for a) surgical HF apparatus (comprising an electrical current source/HF generator and an electrosurgical instrument), which control unit is adapted to be connected to an HF generator/an electrical current source as a control object, comprising an input device or a port for the input device, by means of which a desired application (specific type of use of the HF apparatus) can be activated (pre-adjusted) or is activated (pre-adjusted) on the side of a user, an output device or a port for the output device for displaying the currently activated/selected application and/or the tissue type and a control port via which the control unit outputs an enabling signal to the HF generator/electrical current source only if each time before the start of an application (treatment cycle) the desired application has been activated on the side of the user again.

The object is further achieved on the part of the device by an electrosurgical HF device comprising an electrosurgical instrument and an HF generator/an electrical current source for generating/providing an HF current, the HF generator being electrically connected to the electrosurgical instrument to deliver the HF current to the instrument due to a user-side activation, and the HF generator being arranged to be in a locked state in which the HF generator can not be activated on the side of the user, to automatically change over to an unlocked state at least by a user-side setting of an application to be carried out with the electrosurgical instrument, in which unlocked state the HF generator can be or is activated on the side of the user, and to automatically change over to the locked state after the user-side activation of the electrosurgical instrument connected thereto (completion of the treatment cycle).

The HF apparatus according to the invention is arranged and suitable in particular for carrying out the method of the invention. The instrument may be of the bipolar or monopolar type.

Among others, the invention achieves the advantage that many different applications can be performed with one HF apparatus while always ensuring the respectively correct setting of process parameters for the respective application. Examples for such applications include a sealing of the intestine, a resection or an anastomosis. The invention further allows applications with different tissue types (small intestine, large intestine, rectum, stomach, esophagus) as well as with different numbers of tissue layers.

According to the invention, the HF metering is automatically controlled and, if required, ended by the HF generator, and not manually by the surgeon any more. The surgeon or user only makes a preliminary setting, preferably on the HF generator, which will then automatically adjust on the basis of said preliminary setting the process parameters which are specific for the respective application, for instance selects them from a database. According to the invention, it is absolutely necessary that, in order to be able to carry out an activation of the HF generator, the user first (and each time afresh) has to select and does select the application to be carried out. An activation of the HF generator on the basis of wrong process parameters or a wrong application, which may result in damage to the patient, can be advantageously prevented, as an activation is only possible if a setting of the apparatus or a selection of an application has been made again (each time prior to an application-specific treatment cycle) on the side of the user. It is also possible to advantageously prevent the setting of the apparatus or the selection of an application from being forgotten which would result in working with wrong settings of the apparatus.

An application in the sense of the present application is to be understood as a specific type of surgical application with which the method or the HF apparatus according to the invention is used or is supposed to be used. Particular process parameters such as current intensity, voltage, frequency, amplitude, amplitude form, duration of the current flow, intensity as well as its progression, cutoff point/completion criteria etc. are linked with the respective application. These process parameters have to be correctly adjusted and used for the respective application in order to be able to ensure a satisfactory result and avoid damages to the patient. Each application has the corresponding process parameters associated in a database, for example. Said database may be deposited in the apparatus or in a memory element in the instrument.

After the generator has been activated, it automatically returns to the locked state after completion of the treatment cycle (e.g. deactivation of the electrosurgical instrument) and stays in this state until the user selects an application again. Only at that time the HF generator will be unlocked again. In this way, it is ensured that the apparatus setting is not forgotten. According to one embodiment of the invention, the HF generator automatically returns to the locked state by or due to the user-side activation in the method step d). According to another embodiment of the invention, provision is made that the HF generator automatically returns to the locked state again if there was no activation for a predefined time period after setting an application. Moreover, the automatic locking, i.e. the return of the HF generator to the locked state (method step e)) may occur after the expiration of a predefined period of time after completion of the last HF application. The generator may also return to the locked state if there is identified a certain number (e.g. two) of subsequent activation requests with the same parameter settings.

The safety means described herein, allowing an activation of the HF generator and hence a supply of an HF current to the electrosurgical instrument is possible only after a user-side input of an application and the HF generator being otherwise locked, can be implemented according to advantageous embodiments of the invention in the form of various designs. The setting and the selection of the respective application can be made on the HF apparatus for instance by pressing a key on a display screen of the HF apparatus (e.g. apparatus menu with and without touchscreen), by voice instruction or voice recognition, by means of a rotary knob (e.g. with a neutral position which has to be addressed between the activations), or on the electrosurgical instrument itself, e.g. by means of a rotary knob (e.g. with a neutral position which has to be addressed between the activations) or by means of keys on the instrument. In one embodiment, the rotary knob for selecting the application may additionally be pressed, whereby the selected HF process can be started or the addressed application can be confirmed.

According to one embodiment, a user-side activation of the HF generator is only possible if the selection of the application and the activation, e.g. by pressing an activation button, occur at the same time. According to a special form of the invention, the selected application is announced by the apparatus. This may make sense if the setting of the apparatus is not made by the surgeon itself but by the OP staff, and advantageously offers the surgeon the possibility to convince himself of the correctness of the selected application prior to the activation of the HF generator. According to a further proposal, it is possible that for specific operational modes in which a plurality of applications are possible with identical or similar parameters, the safety modus can be overridden by an intentional decision of the operator, for instance by a long-lasting operation of the activation device or by a quick double or multiple operation of the activation device.

According to one form of the invention, the described safety may be used only for certain types of instruments. Advantageously, the instrument may be automatically identified during connecting them to the HF apparatus. The safety means is linked in only if this is deposited in the parameters of an instrument memory of the HF apparatus. In this respect, data concerning possible applications may be deposited in the instrument memory as well.

BRIEF DESCRIPTION OF THE DRAWING FIGURES

Further features and advantages of the present invention will be apparent from the following exemplary description of particularly preferred embodiments on the basis of the Figures in which.

DETAILED DESCRIPTION

Figure 4:
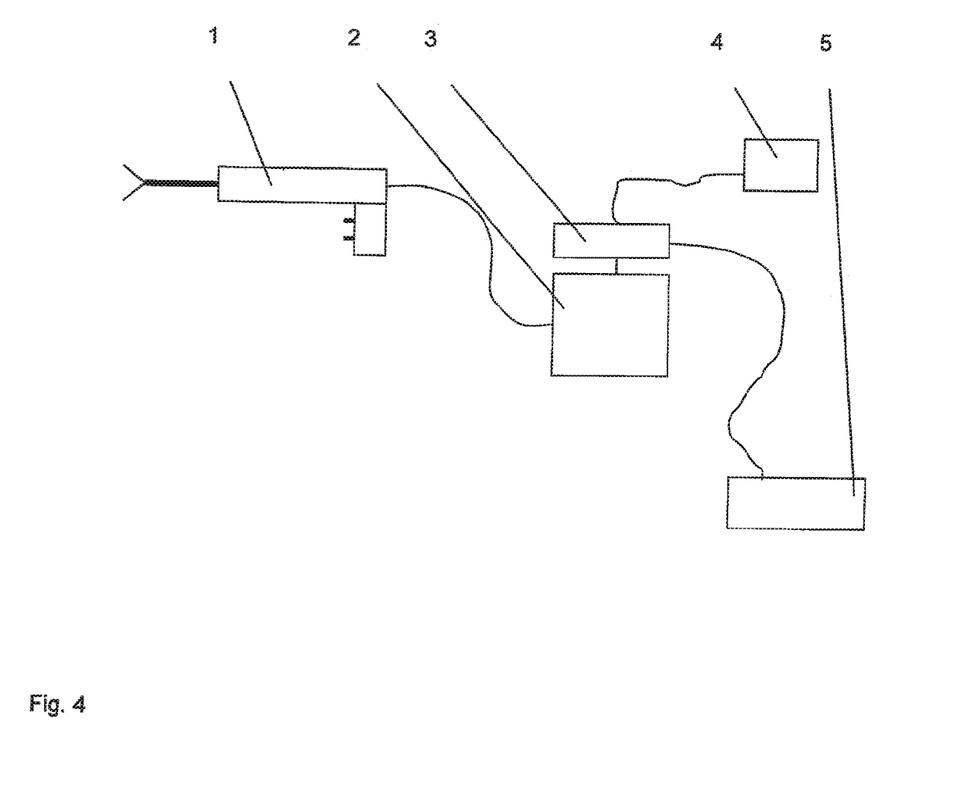

First, an HF apparatus equipped with the present invention is generally described with the aid of FIG. 4.

Accordingly, the HF apparatus comprises an optionally exchangeable electrosurgical instrument 1 of known construction type, for instance a bipolar forceps comprising two scissor branches which can be moved relative to each other and a handle comprising operation keys for selectively applying the scissor branches (or electrodes arranged thereon) with an HF current.

Such an instrument 1 is connected via an electrical conductor cable (bundle) to an electrical current source, e.g. an HF generator or an HF output stage 2 supplying the instrument 1 with an HF current. Further, an input device 5 such as a keyboard and an output device such as a display/monitor 4 are provided. However, it would also be possible to implement the monitor as a so-called touchscreen (combined input/output device). Finally, a control unit 3 is connected to the current source/generator 2, which activates the current source/generator 2 in accordance with specific preconditions for providing a dedicated application-specific HF current and then controls it, if required. The input- and output devices 4, 5 are connected to this control unit 3. It is also conceivable to integrate the input- and output devices 4, 5 in the control unit 3. In general, the components 2, 3, 4 and 5 are installed in an apparatus, i.e. the generator.

Figure 1:
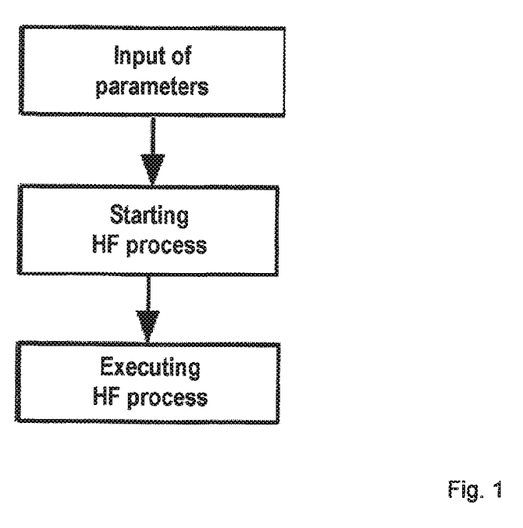
FIG. 1 shows a schematic illustration of the flow of a process activation according to a preferred exemplary embodiment of the invention.

Via the input device 5, the control unit 3 can be set to one of several previously stored, selectable applications (with corresponding operational parameters), as will be explained in the following with the aid of FIGS. 1 to 3. The selected application will then be displayed in the output device 4. The control unit 3 operates the HF generator 2 as a function of parameters, associated to the selected application, according to a specific process flow according to the present invention. FIG. 1 schematically shows the flow of such a process activation.

In a first step, selection variables are input on the side of the user. This input may consist, for example, of selecting a specific application among several possible applications or of selecting certain process parameters. It is only by the input of the respective selection variable or the respective application (as an obligatory measure) that the automatic locking of the HF generator 2 is canceled, so that the latter can be activated or is activated on the side of the user.

Now, in a second step—after selection (and input) of the respective application—the HF process (treatment cycle) is started by a user-side instruction, i.e. the surgical instrument is put into operation and the HF generator 2 is activated, where required. In a third step, the HF process (treatment cycle) is carried out, i.e. the user-selected application is performed, with the corresponding HF current (corresponding to the operational parameters associated to the selected application) being fed to the instrument 1. After this third step, i.e. after completion of the application (treatment cycle) for instance upon deactivation of the electrosurgical instrument 1, the enabling signal is nullified by the control unit 3 and hence the HF generator 2 automatically returns to the locked state in which its user-side activation is not possible without selecting an application and hence producing an enabling signal again.

Figure 2:
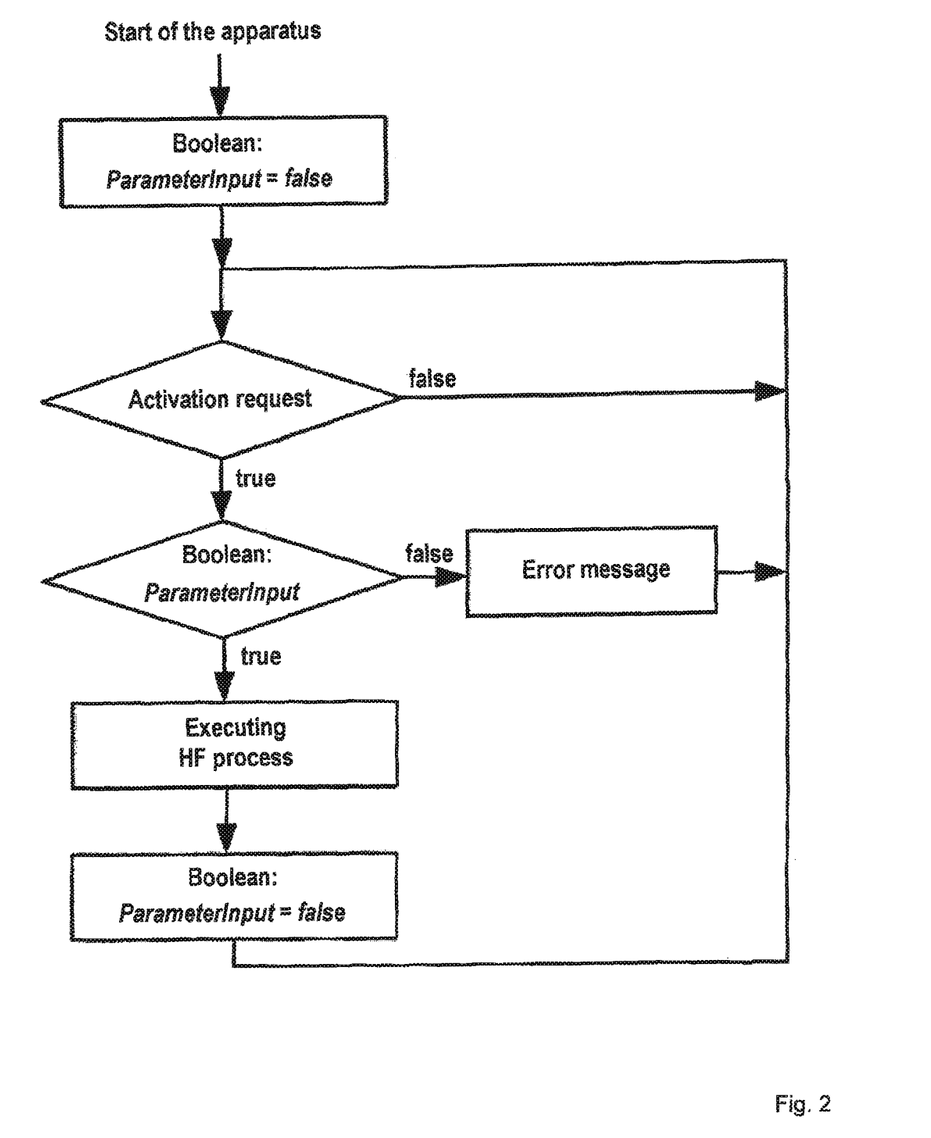
FIG. 2 shows a schematic illustration of a program flowchart relating to an HF activation according to the preferred exemplary embodiment of the invention.

FIG. 2 exemplarily shows a program flowchart for the HF activation. After start-up of the apparatus, the value of a Boolean variable "parameter input" is set to the value "false". This locks the HF generator 2 and, for the time being, it can not be unlocked or activated by the user (for instance by operation of the instrument 1).

Subsequently, a decision is made whether there is an activation request on the part of a user. If there is no activation request (false), the program stays in an endless loop and continues to check if there is an activation desire. If this decision results in "yes" (true), the routine proceeds to the next decision.

In this decision, a verification is made if a selection variable input, i.e. a selection of an application by the user, has been made via the input device. If this decision results in "no" (false), no application has been selected be the user, an error message is output and the routine returns to the initial state in which the variable "parameter input" or "selection input" is set to the value "false". If the decision results in "yes" (true), the HF generator 2 is unlocked, the operational parameters are set in correspondence with the selected application and the routine can carry out the selected HF process after the user-side activation e.g. on the instrument 1.

Having performed/completed the HF process, the Boolean variable "parameter input" is automatically reset to the value "false" and the routine returns to the initial state.

Figure 3:
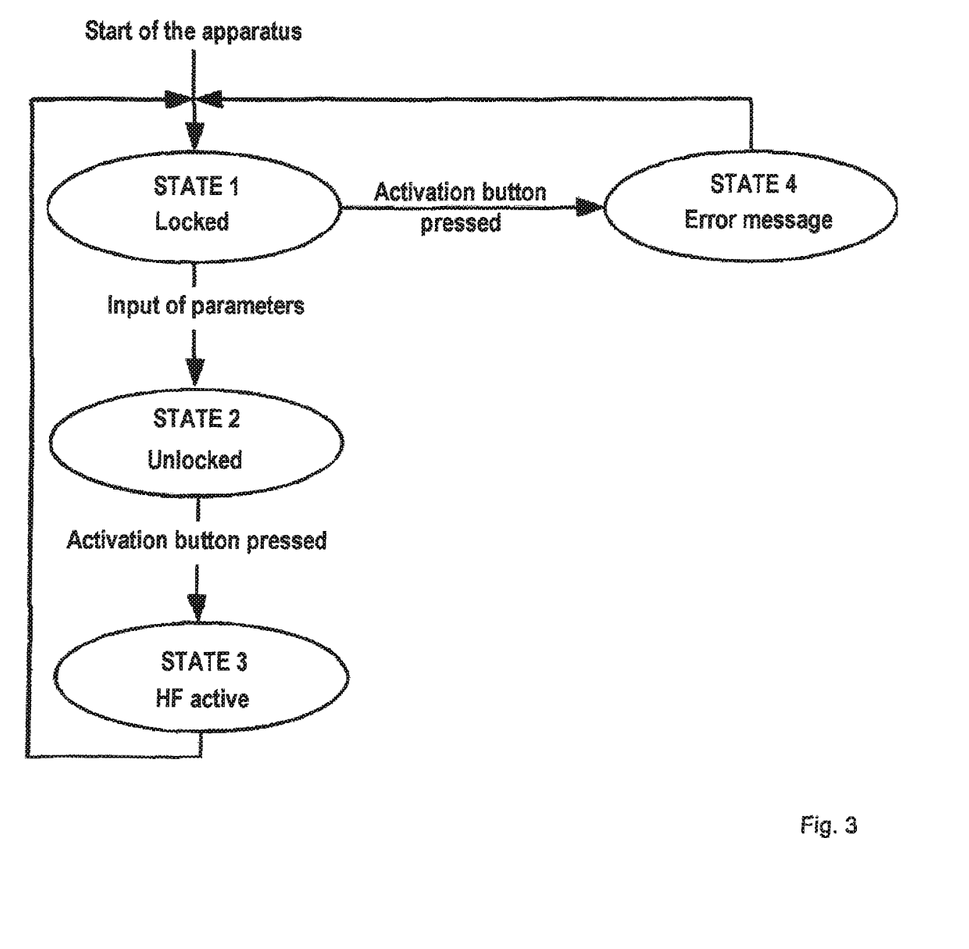
FIG. 3 shows a schematic illustration of a state diagram of an HF activation, and FIG. 4 schematically shows an HF apparatus with which the invention can be applied.

FIG. 3 finally shows schematically a state diagram of the HF activation according to the invention. After the start-up of the apparatus, the state "blocked" or "locked" prevails automatically. This means that the HF generator 2 is in the locked state in which its user-side activation is not possible. If a user gives an activation instruction in this state, for instance by pressing a corresponding activation button, the HF apparatus automatically issues an error message. An activation is not performed.

If there is a parameter input in the blocked (i.e. locked) state by the user for selecting an application to be performed, the system automatically changes over to the released or unlocked state. In this state, the user can perform the activation (once), for instance by pressing an activation button, and the activation is performed, i.e. the HF generator 2 is active and supplies the instrument with an HF current corresponding to the selected application, in order to be locked again after completion of the application.

Finally, it is to be noted that the subject-matter of the invention can be modified or supplemented in various ways.

Accordingly, it is conceivable that the obligatory process of selecting the application does not have to be repeated prior to each treatment cycle but only after a certain number of cycles. This deviation can be associated either to all or only to specific selectable applications. It is also possible that there is an additional safety function such as a timer again canceling the enabling signal after the expiration of a specific time interval after selection of an application, although the treatment cycle has not even started yet.

In summary, the present invention essentially relates to a method and a device for controlling an electrosurgical HF apparatus, in particular an HF apparatus comprising an electrosurgical instrument 1 and an HF generator 2 for generating an HF current, the HF generator 2 being in a locked state in which its activation is not possible, and an application to be carried out is to be selected obligatorily prior to a user-side activation of the HF generator 2, whereby the HF generator 2 is unlocked.

The invention claimed is:

1. A method of controlling an electrosurgical HF high-frequency (HF) apparatus, said HF apparatus comprising an electrosurgical instrument and an HF generator, the HF generator being electrically connected to the electrosurgical instrument to deliver the HF current to the electrosurgical instrument in response to a user-side activation, in which:
   a) the HF generator first is in a locked state in which the HF generator cannot be activated by a user,
   b) starting from step a, an application to be performed with the electrosurgical instrument is obligatorily set by the user,
   c) the HF generator, when step b) has been carried out, automatically changing over to an unlocked state in which the HF generator can be activated by the user,
   d) the HF generator is activated by the user-side activation for carrying out the application to be performed with the electrosurgical instrument,
   e) the HF generator automatically changes over to the locked state after the user-side activation in step d), and
   f) the HF generator automatically changes over to the locked state if it is not activated by the user-side activation during a predefined period of time after the user sets the application to be performed with the electrosurgical instrument.

2. The method according to claim 1, wherein the HF generator in step a) is in the locked state after switching on the HF apparatus or after carrying out the application to be performed with the electrosurgical instrument.

3. The method according to claim 1, wherein the HF generator automatically changes over to the locked state immediately after the user-side activation or upon completion of the user-side activation or after a predefined period of time after the completion of the user-side activation.

4. The method according to claim 1, wherein the electrosurgical instrument connected to the HF generator is automatically identified and is associated to a deposited data record if it does not hold the data record in itself.

5. The method according to claim 4, wherein the data record contains an instruction according to which the change of the HF generator to the locked state in method step e) is suppressed and/or the method step e) is automatically carried out only after an exchange of the electrosurgical instrument.

6. The method according to claim 5, wherein the locked state is canceled if the user-side activation for activating the HF generator is operated for a predetermined time period or a predetermined number of times.

7. The method according to claim 1, wherein an error message or an indication message is outputted if the user attempts the user-side activation of the HF generator in the locked state.

8. An electrosurgical high-frequency (HF) device comprising:
   an electrosurgical instrument; and
   an HF generator for generating an HF current,
   the HF generator being electrically connected to the electrosurgical instrument to deliver the HF current to the electrosurgical instrument in response to a user-side activation,
   the HF generator operable in a locked state in which the HF generator cannot be activated by a user, and an unlocked state in which the HF generator can be activated by the user, the HF generator being configured to automatically switch to the unlocked state after selection of a user-side input of an application type to be performed by the electrosurgical instrument, the HF generator being configured to automatically switch to the locked state after the HF generator is activated by the user for carrying out the application type to be performed by the electrosurgical instrument, and the HF generator being configured to automatically switch to the locked state after the HF generator has not been activated by the user during a pre-defined period of time after the user sets the application type to be performed by the electrosurgical instrument.

9. The electrosurgical HF device according to claim 8, further comprising a plurality of electrosurgical instruments connectable to the HF generator, wherein the plurality of electrosurgical instruments comprises the electrosurgical instrument.

10. The electrosurgical HF device according to claim 8, comprising an operating unit for the selection of the user-side input of the application type to be performed by the electrosurgical instrument or of process parameters, the operating unit being realized as a keyboard, keys, a slide- or toggle switch, a display screen, a rotary knob or a voice instruction/recognition system.

11. The electrosurgical HF device according to claim 10, wherein the operating unit is arranged on the HF generator or on the electrosurgical instrument, or the operating unit is a component of the HF generator or the electrosurgical instrument.

12. The electrosurgical HF device according to claim 8, wherein the electrosurgical instrument is configured to be automatically identified and associated with a data record upon being connected to the HF generator.

13. The electrosurgical HF device according to claim 12, wherein the data record contains an instruction to suppress the switch of the HF generator to the locked state after the user-side activation and/or automatically carry out, only after an exchange of the electrosurgical instrument, the switch of the HF generator to the locked state after the user-side activation.

14. The electrosurgical HF device according to claim 13, wherein the HF generator is configured to return to the locked state if the HF generator is operated for a second predefined period of time after a last user-side activation or a predetermined number of times of subsequent user-side activations.

15. The electrosurgical HF device according to claim 8, wherein the HF generator is configured to be in the locked state after switching on the HF generator or after carrying out the application type to be performed by the electrosurgical instrument.

16. The electrosurgical HF device according to claim 8, wherein an error indication message is outputted when the user attempts to activate the HF generator in the locked state.

17. An electrosurgical high-frequency (HF) device comprising:
an electrosurgical instrument; and
an HF generator for generating an HF current,
the HF generator being electrically connected to the electrosurgical instrument to deliver the HF current to the electrosurgical instrument in response to a user-side activation,
the HF generator operable in a locked state in which the HF generator cannot be activated by a user, and an unlocked state in which the HF generator can be activated by the user,
the HF generator being configured to automatically switch to the unlocked state in response to the user selecting a procedure to be performed by the electrosurgical instrument from a plurality of stored procedures via an input device,
the HF generator being configured to automatically switch to the locked state after the HF generator is activated by the user for carrying out the procedure to the performed by the electrosurgical instrument, and
the HF generator being configured to automatically switch to the locked state after the HF generator has not been activated by the user-side activation during a pre-defined period of time after the user sets the procedure to be performed by the electrosurgical instrument.

* * * * *